United States Patent [19]
Otsubo et al.

[11] Patent Number: 5,916,206
[45] Date of Patent: *Jun. 29, 1999

[54] ABSORBENT PANTS TYPE UNDERGARMENT HAVING DIFFERENTLY TENSIONED ELASTIC ELEMENTS FOR IMPROVED LEAKAGE PREVENTION AND COMFORT

[75] Inventors: Toshifumi Otsubo, Ehime-ken; Hiroyuki Soga, Kagawa-ken, both of Japan

[73] Assignee: Uni-Charm Corporation, Ehime-ken, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/683,544

[22] Filed: Jul. 15, 1996

[30] Foreign Application Priority Data

Jul. 14, 1995 [JP] Japan ................................. 7-178681

[51] Int. Cl.$^6$ ....................................................... A61F 13/15
[52] U.S. Cl. ........................ 604/385.2; 604/393; 604/396
[58] Field of Search ............................. 604/385.1, 385.2, 604/393, 394, 396

[56] References Cited

U.S. PATENT DOCUMENTS

| | | |
|---|---|---|
| 4,685,915 | 8/1987 | Hasse et al. . |
| 5,449,353 | 9/1995 | Watanabe et al. ................... 604/385.2 |
| 5,746,731 | 5/1998 | Hisada ..................................... 604/396 |
| 5,749,865 | 5/1998 | Yamamoto et al. ..................... 604/396 |
| 5,817,087 | 10/1998 | Takabayashi et al. .................. 604/393 |

FOREIGN PATENT DOCUMENTS

| | | |
|---|---|---|
| 0 641 552 | 3/1985 | European Pat. Off. . |
| 0 183 668 | 6/1986 | European Pat. Off. . |
| 0 249 405 | 12/1987 | European Pat. Off. . |
| 0 321 732 | 11/1988 | European Pat. Off. . |
| 4-166150 | 6/1992 | Japan . |
| 4-289201 | 10/1992 | Japan . |
| 4371147 | 12/1992 | Japan ................................. 604/385.2 |
| 4371148 | 12/1992 | Japan ................................. 604/385.2 |
| WO93/17648 | 9/1993 | WIPO . |
| WO96/11657 | 4/1996 | WIPO . |

*Primary Examiner*—Mark O. Polutta
*Attorney, Agent, or Firm*—Lowe Hauptman Gopstein Gilman & Berner

[57] ABSTRACT

In a diaper as one embodiment of a disposable absorbent undergarment according to the invention, the diaper is provided around a front region thereof with a plurality of elastic elements The number of the elastic elements arranged in an area defined by respective vertical widths of 10 mm above and below a front edge of an absorbent core disposed between top- and backsheets is greater than that of the elastic element in the remaining area of the front region. An elongation stress of the elastic elements in the area mentioned firstly is lower than that of the elastic elements in the area mentioned lastly.

3 Claims, 2 Drawing Sheets

ABSORBENT PANTS TYPE UNDERGARMENT HAVING DIFFERENTLY TENSIONED ELASTIC ELEMENTS FOR IMPROVED LEAKAGE PREVENTION AND COMFORT

BACKGROUND OF THE INVENTION

The present invention relates to disposable absorbent pants type undergarments such as disposable pants type diapers for babies, incontinent pants, training pants for babies and the like.

In conventional absorbent pants type undergarments, a waist-opening and a pair of leg-openings are usually provided with respective elastic members to impart to the respective opening edges a desired stretchability in the circumferential direction. The elastic elements associated with the waist-opening are usually arranged over a considerably large region defined between an edge of the waist-opening and a crotch region extending between the waist-opening and leg-openings. These elements exert a pressure upon a region of the undergarment overlying a liquid-absorbent core to thereby bring an inner side of this region tightly against the wearer's body. Such an undergarment is disclosed, for example, in Japanese Laid-Open Patent Application Nos. Hei4-166150 and Hei4-289201.

Attempts to bring this desired region of the undergarment overlying the liquid-absorbent core tightly against the wearer's body to thereby avoid leakage of body fluids disadvantageously causes the elastic elements to compress the wearer's waist over a wide range and creates an uncomfortable feeling of wear.

Surprisingly, it has been found that leakage of body fluids can be effectively avoided by bringing only a local area overlying the longitudinally opposite edges of the core rather than the entire region overlying the core closely against the wearer's body to alleviate the aforementioned uncomfortable feeling.

Accordingly, a principal feature of the invention is to arrange, in a disposable absorbent pants type undergarment, elastic elements associated with the waist in a region adjacent each of longitudinally opposite edges of the core with a relatively high density so that fitness of this region to the wearer's skin may be at least partially improved.

SUMMARY OF THE INVENTION

According to the invention, there is provided a disposable absorbent pants type undergarment comprising a liquid-permeable topsheet, a liquid-impermeable backsheet and a liquid-absorbent core disposed therebetween. The undergarment has a front region, a rear region and a crotch region extending therebetween. A plurality of elastic elements extend around a waist portion and around a pair of leg-openings, respectively, of the undergarment. In accordance with the invention, the core extends longitudinally into the front and rear regions and has front and rear edges spaced apart from each of the waist-opening edges of the front and rear regions, respectively. The elastic elements associated with the front region are arranged between the front edge of the core and the waist-opening edge of the front region and between the front edge of the core and the crotch region. The number of the elastic elements arranged in a first area defined by respective vertical widths of 10 mm above and below the front edge of the core is greater than that of the elastic elements arranged in a second area of the front region excluding the first area, and an elongation stress of each of the elastic elements in the first area is lower than that of the elastic elements in the second area.

According to the present invention, there is also provided a disposable absorbent undergarment which comprises the elastic elements associated with the rear region being arranged between the rear edge of the core and the waist-opening edge of the rear region and between the rear edge of the core and the crotch region. The number of elastic elements arranged in a third area defined by respective vertical widths of 10 mm above and below the rear edge of the core is greater than that of the elastic elements arranged in a fourth area of the rear region excluding the third area. An elongation stress of each of the elastic elements in the third area is lower than that of the elastic elements in the fourth area.

With the disposable absorbent undergarment constructed as described above, the location of the undergarment overlying the area defined by the front edge of the core and adjacent thereto has a comfortable fit to the wearer's body without exerting a relatively high pressure since the elastic elements associated with the front region are arranged in this area with a relatively high density, but with a relatively lower elongation stress.

DESCRIPTION OF THE PREFERRED EMBODIMENT

Figure 1:
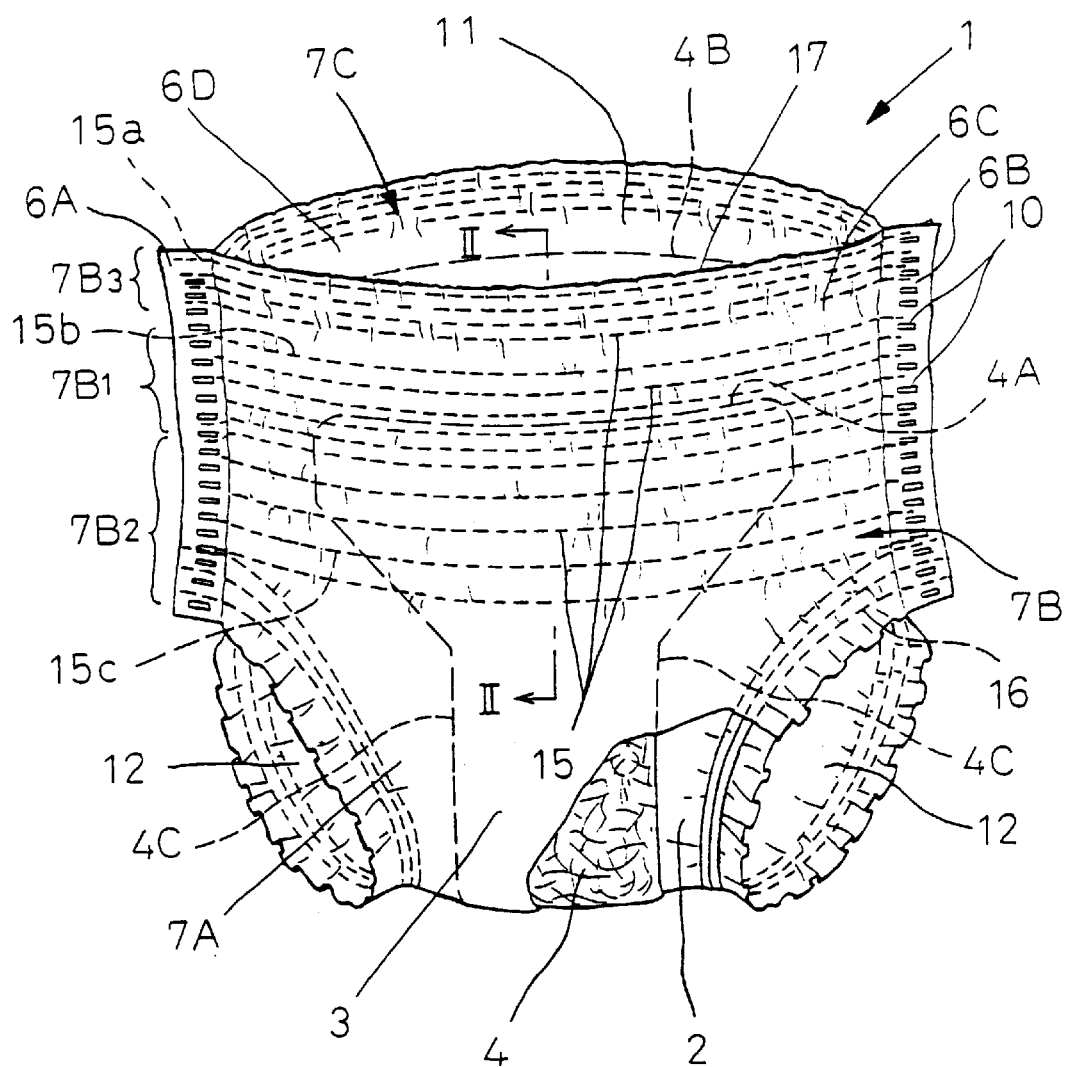
FIG. 1 is a perspective view showing a diaper of pants type according to the invention as partially broken away.

Referring to FIG. 1, a diaper comprises a liquid-permeable topsheet 2, a liquid-impermeable backsheet 3 and a liquid-absorbent core 4 disposed between these two sheets 2, 3 and further comprises a front region 5, a rear region 6 and a crotch region 7 extending between these two regions 5, 6 as viewed longitudinally of the diaper 1. The topsheet and backsheet 2, 3 are bonded together at their portions extending outward beyond a peripheral edge of the core 4 and the front and rear regions 5, 6 have their inner surfaces opposed to each other bonded together along their transversely opposite edges at intermittently provided adhesive spots 10 to define a waist-opening 11 and a pair of leg-openings 12 and thereby configure the diaper 1 as a whole in the form of a pants (or briefs) -shape. In the diaper 1, the core 4 extends longitudinally over the crotch region 7 into the front and rear regions 5, 6, and has a front edge 4A, a rear edge 4B and transversely opposite edges 4C. The diaper 1 is provided around at least the front region 5 with a first elastic member 15 and around each leg-opening with a second elastic member 16. The first and second elastic members 15, 16 are secured in a stretched condition to an inner surface of at least one of the topsheet and backsheet 2, 3 so that a number of gathers may be formed around the waist and the legs as these elastic members 15, 16 contract.

Figure 2:
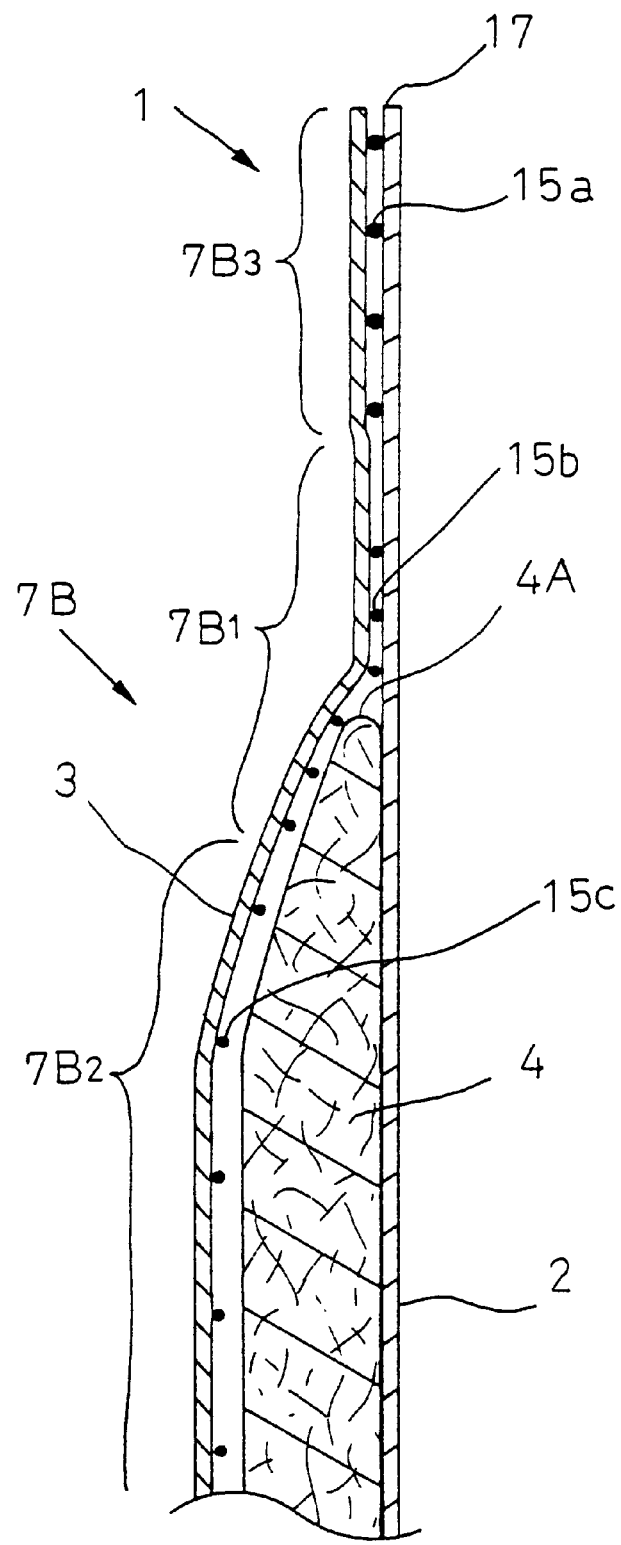
FIG. 2 is a sectional view taken along a line II—II in FIG. 1.

Referring to FIG. 2, the core 4 has a thickness which is substantially uniform over the front region 5, but over an area of at least 10 mm wide adjacent the front edge 4A, is progressively reduced toward the front edge 4A. Such a locally reduced thickness may be obtained either by reducing the core material progressively toward the front edge 4A or by compressing the core material in this front edge area. The portions of the topsheet and backsheet 2, 3 extending outward beyond the front edge 4A are bonded together by means of hot melt adhesive (not shown) to form a waist-opening edge 22. The rear region 6 is also constructed in a manner substantially similar to that shown in FIG. 2.

Referring again to FIGS. 1 and 2, the first elastic member 15 comprises a group 17B$_3$ of elastic elements 15a extending along the opening edge 22, a group 17B$_1$ of elastic elements 15b extending adjacent the front edge 4A of the core 4 and a group 17B$_2$ of elastic elements 15c extending below the group 17B$_1$ of elastic elements 15b. Each elastic element 15a of group 17B$_3$ is 0.5 to 3 mm wide and 0.05 to 1.5 mm thick. Each elastic element 15b of the group 17B$_1$ is 0.1 to 1.5 mm wide and 0.05 to 1.5 mm thick. Each elastic element 15c of the group 17B$_2$ is 0.1 to 5 mm wide and 0.05 to 1.5 mm thick. The elastic elements 15b, 15c of the groups 17B$_1$ and 17B$_2$ intersecting the core 4 are bonded to the backsheet 3 so that they may be distributed on an outer surface of the core 4. The elastic elements 15a, 15b, 15c of the groups 17B$_3$, 17B$_1$ and 17B$_2$ are secured to the backsheet 3 with a 50% elongation stress per 150 mm of 5 to 50g and an elongated ratio of 1.1 to 2.5. The second elastic member 16 comprises a group 17A of elastic elements 16a. The elongation stress of each of the elastic elements 15b of the group 17B$_1$ is lower than that of each of the elastic elements 15a, 15c of the groups 17B$_3$, 17B$_2$.

With the diaper 1 constructed as described above, the core 4 closely fits the wearer's skin at the front edge 4A and an area adjacent thereto, since the elastic elements 15b of the group 17B$_1$ are densely arranged above and below the front edge 4A of the core 4. Consequently, even if a portion of discharged body fluids flows on an upper surface of the topsheet 2 without being absorbed by the core 4, such flow will be unable to pass through the area adjacent the front edge 4A and therefore reliably prevented from leaking outward. In the diaper 1, the elastic elements 15a of the group 17B$_3$ extend transversely across the front and rear regions 5, 6 so that they are continuous from the front region 5 to the rear region 6. Furthermore, an area defined by the group 17B$_1$ including the elastic elements 15b will not exert a great pressure against the center zone of the wearer's stomach and will therefore be comfortable to wear, compared with the groups 17B$_3$, 17B$_2$ including the elastic elements 15a, 15c, since the elongation stress of each of the elastic elements 15b of the group 17B$_1$ is lower than that of each of the elastic elements 15a, 15c of the groups 17B$_3$, 17B$_2$. While the elastic elements 15b, 15c of the groups 17B$_1$, 17B$_2$ are preferably arranged both on the front region 5 and on the rear region 6, it is also possible without departing from the scope of the invention to arrange them on only one of these front and rear regions, for example, depending on the wearer's particular body form.

The elastic elements 15b of the group 17B$_1$ may be replaced by one or more relatively wide ribbon-like elastic member(s) to improve fitness of the core at its front edge 4A and the area therearound to the wearer's skin. However, such replacement would be disadvantageous in that a desired air-permeation between in- and exterior of the diaper 1 will be significantly impeded.

In order to implement the invention, a nonwoven fabric or perforated plastic film may be used for the topsheet 2 and a plastic film such as polyethylene may be used for the backsheet 3. Fluff pulp alone or a mixture of fluff pulp and superabsorptive polymer powder may be molded by any well known technique into a shape required for the core 4. A material having a rubber-like elasticity such as rubber or plastic elastomer may be used for the first and second elastic members 15, 16.

With the undergarment of the invention, the undergarment reliably fits the wearer's body and can prevent body fluids from leaking beyond this edge without deteriorating comfort. Furthermore, the progressive reduction of thickness of the core adjacent the front and/or rear edge(s) thereof is effective to reduce a difference in level generated between the core and the wearer's skin and thereby improve a wearing appearance. Even if such progressive decrease in the core thickness is obtained by compressing the core material, the densely arranged elastic elements allow such progressively thinned area to fit the wearer's body.

What is claimed is:

1. A disposable absorbent pants type undergarment comprising a liquid-permeable topsheet, a liquid-impermeable backsheet joined to the topsheet and a liquid-absorbent core disposed therebetween, and jointly defining a front region, a rear region and a crotch region extending therebetween, and a plurality of elastic elements extending around said front and rear regions and around a pair of leg-openings, respectively, wherein the improvement comprises:

said core extending longitudinally into said front and rear regions and having front and rear edges spaced apart from each of waist-opening edges of said front and rear regions, respectively;

said elastic elements associated with said front region being arranged between the front edge of said core and the waist-opening edge of said front region and between the front edge of said core and said crotch region, the number of said elastic elements arranged in a first area defined by respective vertical widths of 10 mm above and below the front edge of said core being greater than that of said elastic flements arranged in a second area of said front region excluding said first area, an elongation stress of each of said elastic elements in said first area being lower than that of said elastic elements in said second area.

2. The undergarment according to claim 1, wherein, in an area of said core at least 10 mm inward from the front edge of said core, said core has a thickness progressively reduced toward said front edge.

3. The undergarment according to claim 1, wherein said undergarment further comprises: said elastic elements associated with said rear region being arranged between the rear edge of said core and the waist-opening edge of said rear region and between the rear edge of said core and said crotch region, the number of said elastic elements arranged in a third area defined by respective vertical widths of 10 mm above and below the rear edge of said core being greater than that of said elastic elements arranged in a fourth area of said rear region excluding said third area, an elongation stress of each of said elastic elements in said third area being lower than that of said elastic elements in said fourth area.

\* \* \* \* \*